United States Patent
Scripka et al.

(10) Patent No.: US 12,347,534 B2
(45) Date of Patent: Jul. 1, 2025

(54) SYSTEM AND METHOD FOR IMPLEMENTING A MEDICAL RECORDS ANALYTICS PLATFORM

(71) Applicant: KPMG LLP, New York, NY (US)

(72) Inventors: David Scripka, Atlanta, GA (US);
Drew S. Cobb, Ashburn, VA (US);
Thomas R. Covella, II, Denver, CO (US); Dylan Kab, Raleigh, NC (US);
Martin Kaestner, Bethesda, MD (US);
Rachel Wagner-Kaiser, Seattle, WA (US)

(73) Assignee: KPMG LLP, New York, NY (US)

( * ) Notice: Subject to any disclaimer, the term of this patent is extended or adjusted under 35 U.S.C. 154(b) by 316 days.

(21) Appl. No.: 17/812,474

(22) Filed: Jul. 14, 2022

(65) Prior Publication Data
US 2023/0017211 A1      Jan. 19, 2023

Related U.S. Application Data

(60) Provisional application No. 63/221,561, filed on Jul. 14, 2021.

(51) Int. Cl.
*G06F 40/30*    (2020.01)
*G06F 40/20*    (2020.01)
*G16H 10/60*    (2018.01)
*G16H 30/40*    (2018.01)

(52) U.S. Cl.
CPC ............ *G16H 10/60* (2018.01); *G06F 40/20* (2020.01); *G06F 40/30* (2020.01); *G16H 30/40* (2018.01)

(58) Field of Classification Search
None
See application file for complete search history.

(56) References Cited

U.S. PATENT DOCUMENTS

| | | | |
|---|---|---|---|
| 10,846,341 B2 | 11/2020 | Cerino et al. | |
| 11,321,364 B2 | 5/2022 | Lee et al. | |
| 2016/0335524 A1* | 11/2016 | Bremer | G06F 18/214 |
| 2018/0183995 A1* | 6/2018 | Barnett | H04L 67/02 |
| 2020/0160510 A1 | 5/2020 | Lindemer et al. | |
| 2021/0081601 A1 | 3/2021 | Begun et al. | |
| 2021/0089589 A1 | 3/2021 | Cerino et al. | |

OTHER PUBLICATIONS

International Bureau, International Application No. PCT/US22/37072, PCT Notification of the International Search Report and Written Opinion, Nov. 16, 2022, pp. 1-18.

\* cited by examiner

*Primary Examiner* — Quynh H Nguyen
(74) *Attorney, Agent, or Firm* — Hunton Andrews Kurth LLP

(57) ABSTRACT

The invention relates to computer-implemented systems and methods for analyzing medical images and records in various formats and structures from disparate sources and providers to provide answers to specific medical-related questions. An embodiment of the present invention is directed to accessing a health care form, identifying related text, leveraging computer vision technology to group nearby text, and applying deep learning models to identify fields from the text. This information may then be used to create a structured standardized output.

20 Claims, 3 Drawing Sheets

SYSTEM AND METHOD FOR IMPLEMENTING A MEDICAL RECORDS ANALYTICS PLATFORM

CROSS-REFERENCE TO RELATED APPLICATION

This application claims priority to U.S. Provisional Application Ser. No. 63/221,561, filed Jul. 14, 2021, the contents of which are incorporated by reference herein in their entirety.

This application is related to U.S. patent application Ser. No. 17/100,019, filed on Nov. 20, 2020, which is a continuation application of U.S. patent application Ser. No. 16/159,088, filed on Oct. 12, 2018, now U.S. Pat. No. 10,846,341, which claims the benefit of U.S. Provisional Patent Application Ser. No. 62/572,266, filed on Oct. 13, 2017, the contents of which are incorporated by reference herein in their entirety.

This application is related to U.S. patent application Ser. No. 16/730,131, filed on Dec. 30, 2019, now U.S. Pat. No. 11,321,364, which is a continuation-in-part application of U.S. patent application Ser. No. 16/159,088, filed on Oct. 12, 2018, now U.S. Pat. No. 10,846,341, which claims the benefit of U.S. Provisional Patent Application Ser. No. 62/572,266, filed on Oct. 13, 2017, the contents of which are incorporated by reference herein in their entirety.

FIELD OF THE INVENTION

The present invention relates to systems and methods for automated analysis of structured and unstructured data, and more particularly to analysis of medical images and records in various formats and structures from disparate sources and providers.

BACKGROUND

The digitization of labor continues to progress as advancements in machine learning, natural language processing, data analytics, mobile computing and cloud computing are used in various combinations to replace certain business processes and functions. Basic process automation can be implemented without significant IT investment as solutions may be designed, tested and implemented at a relatively low cost. Enhanced process automation incorporates more advanced technologies that enable the use of data to support elements of machine learning. Machine learning tools can be used to discover naturally-occurring patterns in data and to predict outcomes. And natural language processing tools are used to analyze text in context and extract desired information.

However, such digital tools alone do not create a solution for many complex business problems. For example, such tools are generally found in a variety of formats and coding languages and are not specific to any particular business problem. Hence, they are difficult to integrate and they are often not customized. As a result, in many cases these tools are not particularly useful to a company or other organization because there is a large gap between the various tools that are available and what the company really needs, i.e., an automated solution or answer to a specific business question (e.g., "Which of these 500 medical records fails to comply with new privacy regulation XYZ?"). This is particularly relevant in the medical field as medical records and images are managed in different formats by various providers, medical offices, hospitals, clinics, etc. Oftentimes, medical questions require analysis through multiple different records managed by many disparate systems and platforms.

It would be desirable, therefore, to have a system and method that could overcome the foregoing disadvantages of known systems and that could apply automated and customized analysis to analyze documents, communications, text files, websites, and other structured and unstructured input files to generate output in the form of answers to specific questions and other supporting information.

SUMMARY

According to one embodiment, the invention relates to a computer-implemented method for analysis of structured and unstructured data to provide answers to specific medical-related questions. The method may comprise the steps of: identifying at least one question and at least one input file to be analyzed, wherein the at least one input file relates to a medical record wherein the medical record comprises medical history data for a patient over a predetermined period of time; applying text spatial analysis and clustering of related and nearby text to the at least one input file based on one or more similarity measures; and responsive to the text spatial analysis and clustering, applying an artificial intelligence process to the at least one input file, the artificial intelligence process comprising the steps of: generating, for the at least one input file, a converted file in a data format that is standardized for a plurality of input file types and a plurality of data providers and that includes at least one element; wherein the at least one element is associated with a key identifier and a corresponding value; generating at least one expression, wherein the expression comprises an expression string in a domain-specific language; reading, via a machine review portion of the artificial intelligence process, the at least one expression; and applying, via the machine review portion of the artificial intelligence process, the at least one expression to the converted file to automatically generate a structured data output responsive to the at least one question.

According to another embodiment, the invention relates to a computer-implemented system for analysis of structured and unstructured data to provide answers to specific medical-related questions. The system may comprise: an input that identifies at least one question and at least one input file to be analyzed, wherein the at least one input file relates to a medical record wherein the medical record comprises medical history data for a patient over a predetermined period of time; and a server configured to perform the steps of: applying text spatial analysis and clustering of related and nearby text to the at least one input file based on one or more similarity measures; responsive to the text spatial analysis and clustering, applying an artificial intelligence process to the at least one input file; generating, for the at least one input file, a converted file in a data format that is standardized for a plurality of input file types and a plurality of data providers and that includes at least one element; wherein the at least one element is associated with a key identifier and a corresponding value; generating at least one expression, wherein the expression comprises an expression string in a domain-specific language; reading, via a machine review portion of the artificial intelligence process, the at least one expression; and applying, via the machine review portion of the artificial intelligence process, the at least one expression to the converted file to automatically generate a structured data output responsive to the at least one question.

The invention also relates to a computer-implemented system for analysis of structured and unstructured data to provide answers to a specific business and/or medical questions, and to a computer-readable medium containing program instructions for executing a method for analysis of structured and unstructured data associated with medical records and/or other patient data.

The system may provide value in a number of ways including: (a) providing 100% or near 100% coverage vs. traditional sampling approaches; (b) reducing costs and development time needed to produce insights; (c) enabling humans to achieve and manage precise consistency; (d) leveraging the knowledge and experience of subject matter experts such as medical professionals; and (e) automatically creating audit logs describing how data has been processed.

These and other advantages will be described more fully in the following detailed description.

BRIEF DESCRIPTION OF THE DRAWINGS

In order to facilitate a fuller understanding of the present invention, reference is now made to the attached drawings. The drawings should not be construed as limiting the present invention, but are intended only to illustrate different aspects and embodiments of the invention.

DETAILED DESCRIPTION

Figure 1:
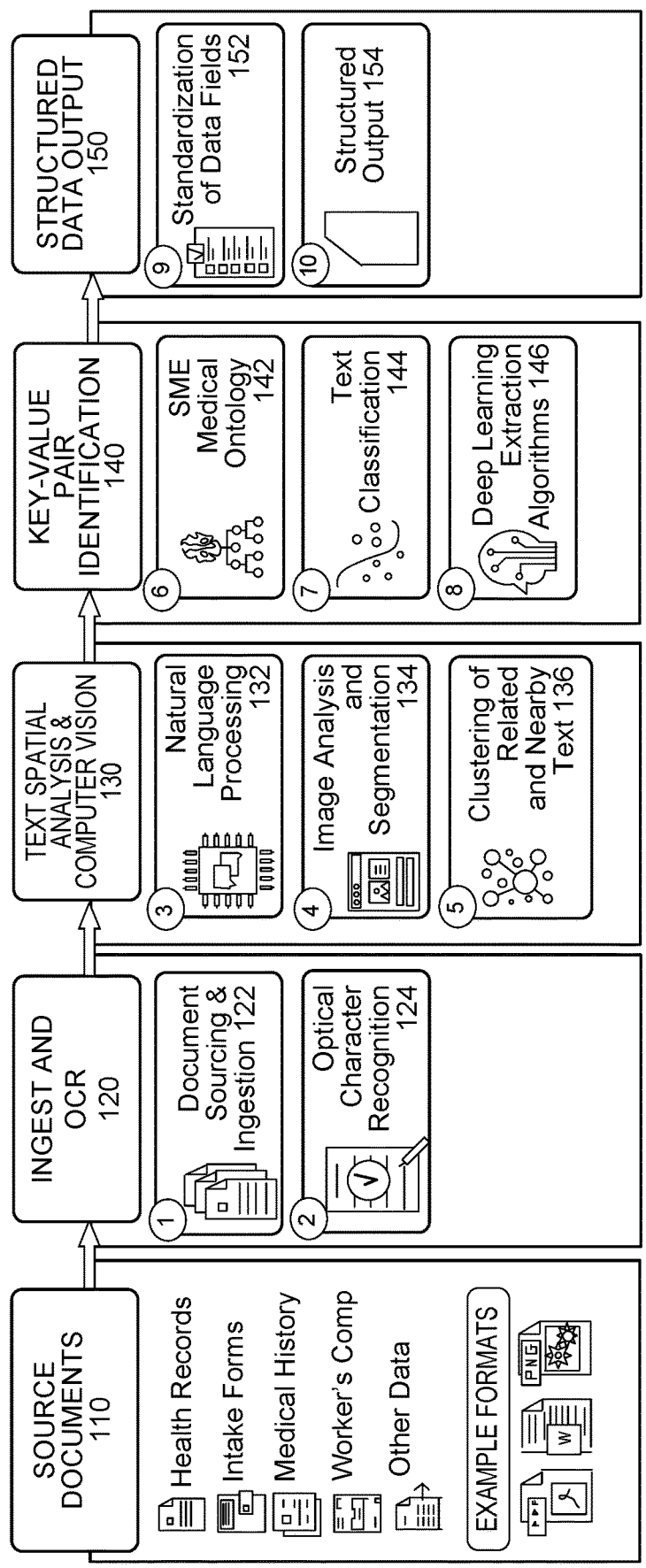
FIG. 1 is an exemplary workflow, according to an embodiment of the present invention.

Exemplary embodiments of the invention will now be described in order to illustrate various features of the invention. The embodiments described herein are not intended to be limiting as to the scope of the invention, but rather are intended to provide examples of the components, use, and operation of the invention.

According to an embodiment, the invention relates to an automated system and method for analysis of structured and unstructured data relating to medical records. The analysis system (sometimes referred to herein as the "System") may include a portfolio of artificial intelligence capabilities, including artificial intelligence domain expertise and related technology components. The System may include foundational capabilities such as document ingestion and optical character recognition (OCR), e.g., the ability to take documents and convert them into formats readable by a machine to perform analytics. According to an embodiment of the present invention, the System may also include machine learning components that provide the ability to learn without being explicitly programmed (supervised and unsupervised); deep learning components that model high-level abstractions in data; and natural language processing (NLP) and generation, e.g., functionality to understand human speech or text and produce text or speech.

The System may also be designed to ingest and process various types of input data, including structured data (e.g., data organized in columns and rows such as transactional system data and Microsoft Excel files); semi-structured data (e.g., text not stored in a recognized data structure but that still contains some type of tabs or formatting, such as forms); unstructured data (e.g., text not stored in a recognized data structure, such as contracts, Tweets and policy documents); and images (e.g., photographs, images and/or other visual depictions of physical objects, human body/organs, etc.) and voice (e.g., human voice data).

Images may represent medical images encompassing X-rays, CT (computed tomography) scan, MRI (magnetic resonance imaging), ultrasound, nuclear medicine imaging, positron-emission tomography (PET), arthrograms, myelograms, elastography images, photoacoustic imaging, tomography, echocardiography, functional near-infrared spectroscopy, magnetic particle imaging, multi-dimensional images, etc. Analysis of medical images enable medical professionals to make accurate diagnosis of various conditions and support proper treatments. Medical images may also include measurement data, graphs, charts and other representations produced through techniques such as electroencephalography (EEG), magnetoencephalography (MEG), electrocardiography (ECG), and others. Medical images may include other representations, techniques and processes of imaging the interior of a body and other visual representations of organs or tissues. Other forms and types of medical images and/or media data may be supported.

The System may be deployed to ingest, understand and analyze the documents, communications, images and websites that make up the rapidly growing body of structured data and unstructured data. According to one embodiment, the System may be designed to: (a) read transcripts, medical records, tax filings, communications, financial reports, payment records, insurance documents and similar documents and input files, (b) extract information and capture the information into structured files, (c) assess the information in the context of policies, rules, regulations, and/or business objectives, treatments, diagnosis, medical research and (d) answer questions, produce insights, and identify patterns and anomalies in the information. The System may capture and store subject matter expertise; ingest, mine and classify documents using natural language processing (NLP); incorporate advanced machine learning and artificial intelligence methods; and utilize collaborative, iterative refinement with advisory and client stakeholders.

Examples of questions that the system can answer may include, for example, which medical records comply with a certain policy or regulation (e.g., patient privacy laws, HIPAA, HITECH, social security act, false claims act, patient protection and affordable care act, etc.); which treatment plans are most safe, risky, effective, promising; which claims warrant intervention/investigation; which documents are experiencing a change in trend or meaning, etc. Examples of policies or rules that the System can analyze may include, for example, new regulations, standards, targets, assessment of risk, patient safety compliance, privacy of patient information, billing practices, corporate compliance, and/or settlement outcomes, to name a few. Examples of documents that the system can analyze may include, for example, medical records, health records, intake forms, medical history, worker's compensation, insurance policies, insurance claims notes, customer service transcripts, email exchanges, health/exercise service providers, health/exercise monitoring apps and platforms, etc. Other forms of data and information may be captured.

An embodiment of the present invention is directed to analyzing and processing medical records, data and/or other information and further leveraging technology described in U.S. Pat. Nos. 10,846,341 and 11,321,364, which are incorporated by reference in their entirety.

Medical records generally refer to data and/or documentation relating to a patient's medical history and care. Medical records may include a variety of information entered by healthcare professionals. This may include observations and administration of drugs and therapies, test results, x-rays, reports, medical history, etc. Medical records may also include images, recordings, electronic data, various forms of data, etc. Medical history may provide a longitudinal record to a patient since birth or an earliest medical event. Medical history may chronicle diseases, illnesses, growth landmarks, etc. Various categories of medical history may include surgical history, obstetric history, medications and medical allergies, family history, social history, habits, immunization history, growth and developmental history, etc. Other medical data may include vaccine history, exercise activity, social media data, mental health history, etc.

Each provider (including medical provider, doctor office, hospital, clinic, research entity, insurance provider, payment service, etc.) may have their own version of how information is collected, documented, structured and/or retained. For example, healthcare providers may vary in how they document certain recommendations, assessments, etc. In addition, each hospital or hospital network may use differing methodologies and systems. An embodiment of the present invention recognizes that the underlying information may be captured and managed in many different ways which further complicates how to extract and/or discern relevant information.

An embodiment of the present invention is directed to analyzing medical records in multiple different variations, formats, structures, etc. and then extracting specific information to generate a specific answer to certain questions. Inquiries may relate to worker's compensations, specific treatments, patient history that could be complicated due to medication, prescribed treatment (e.g., physical therapy, etc.), which part of the body is affected, etc. For example, an exemplary question may refer to whether a worker's compensation claim should be allowed for a particular treatment. Other inquiries may relate to determining whether an injury/condition is related or the same as a previous injury/condition; whether a patient's current work/disability status is appropriate given the patient's current injury/condition; whether the indicated treatment is appropriate given the patient's current injury/condition, etc. Inquiries may also relate to medical research, clinical research, experimental treatments, trends, anomaly detection, etc.

An embodiment of the present invention is directed to applying natural language processing and machine learning (ML) to interpret certain clauses within a medical record and/or other medical document or dataset. Accordingly, medical records and/or other patient data may be processed to obtain specific answers in a predefined specific way. For example, multiple different pieces of information may be analyzed to determine a medical history of the client. Additional logic and interpretation may be applied to provide insights to a patient's history and medical records. This leads to a more accurate diagnosis and effective treatment plan.

Current systems seek to simplify and streamline computer assisted coding. Such solutions are directed to a single encounter and fail to consider a patient's entire longitudinal history. Current technology and developments are limited to an encounter-based environment. An embodiment of the present invention applies analysis against a longitudinal record of what has happened to the patient since birth (or an earliest recorded event).

With the extensive processing and analytics available with an embodiment of the present invention, a patient may be examined in a holistic and comprehensive manner. An embodiment of the present invention applies a longitudinal perspective over an extended period of time and may further involve various different sources of information. For example, a patient's entire history may include an initial emergency room visit, diagnosis of a broken leg, physical therapy, treatment, counseling, etc. The success of each stage may be evaluated and continuously refined based on the patient's healing process as well as treatment options and available resources. Accordingly, an embodiment of the present invention seeks to provide an interpretation and an alignment between a certain injury and a recommended treatment plan having a set of expected outcomes. This may further involve determining that the treatment plan was successful or whether there is a need for refinement.

FIG. 1 is an exemplary workflow, according to an embodiment of the present invention. An exemplary embodiment of the present invention is directed to a platform and system that includes a combination of components such as Optical Character Recognition (OCR), Text Processing, Natural Language Processing, Computer Vision, and Deep Learning. Implementing these capabilities together provides an ability to identify and extract information from very different kinds of medical record documents and disparate sources/systems.

As shown in FIG. 1, Source Documents 110 may include various forms and types of medical data including health records, intake forms, medical history, worker's compensation documents and/or other data. Source documents 110 may be in different formats, structures, languages, etc. Sources may include data from various systems, applications, services, products, etc.

Medical data may include structured, semi-structured and unstructured data. Sources of medical data may include electronic health records (EHRs), electronic medical records (EMRs), genome sequences (DNA), data from health and fitness trackers, equipments, devices and applications (e.g., wearable devices, mobile device apps, exercise equipments, etc.), Medicare and Medicaid data, etc. Medical data may also include data from social media platforms, health and exercise communities, specialists, etc.

An embodiment of the present invention may then ingest data and perform an optical character recognition process as shown by 120. Data from various source documents and platforms may be ingested and processed. Data may be ingested through a Document Sourcing and Ingestion module 122 and further processed through Optical Character Recognition 124 or other electronic conversion of scanned images and text into machine encoded texts for computations and analysis.

Text spatial analysis and computer vision may be applied at 130. Computer vision refers to acquiring, processing, analyzing and understanding digital images and extracting high-dimensional data. This may further involve transformation of visual images into descriptions. As shown in 130, Text spatial analysis and computer vision may involve data processing through Natural Language Processing 132, Image Analysis and Segmentation 134 and Clustering of related and nearby text 136. Text spatial analysis and clustering may refer to a combination of computer vision and NLP approaches to structure/segment an image of a medical record into semantically useful regions. For example, these approaches may be used to identify a "Patient History" section of a medical record based textual and visual indicators, regardless of the exact format and presentation of that content in the medical record.

Key-value pair identification may be performed at 140. Key-value pair identification may involve linking data items where a key is used as a unique identifier for a corresponding value. This may be accomplished through SME (subject matter expert) Medical Ontology 142, Text Classification 144 and Deep Learning Extraction Algorithms 146.

Examples of key-value pair identification and extraction in medical records may include extracting patient information including demographics, medical history, current status, and/or other data when presented in a form/table structure with implicit pairs of such as information type and answer, e.g., Patient Name: John Doe. Another example may include parsing of administrative information about a medical record such as providing health care professional and location, visit date, scheduled follow-up appointments, e.g., Date of Visit: Oct. 10, 2010. Other examples may involve parsing of assessment/treatment related information when presented in a form/table structure with implicit pairs of information type and answer, e.g., Patient Status: Full temporary disability.

Data may be outputted in various formats including structured data output 150. This may involve standardization of data fields 152 and a structured output 154. Structured data output 150 may be communicated to recipients, receiving platforms and/or other systems via a communication network and/or other modes of communication.

Figure 2:
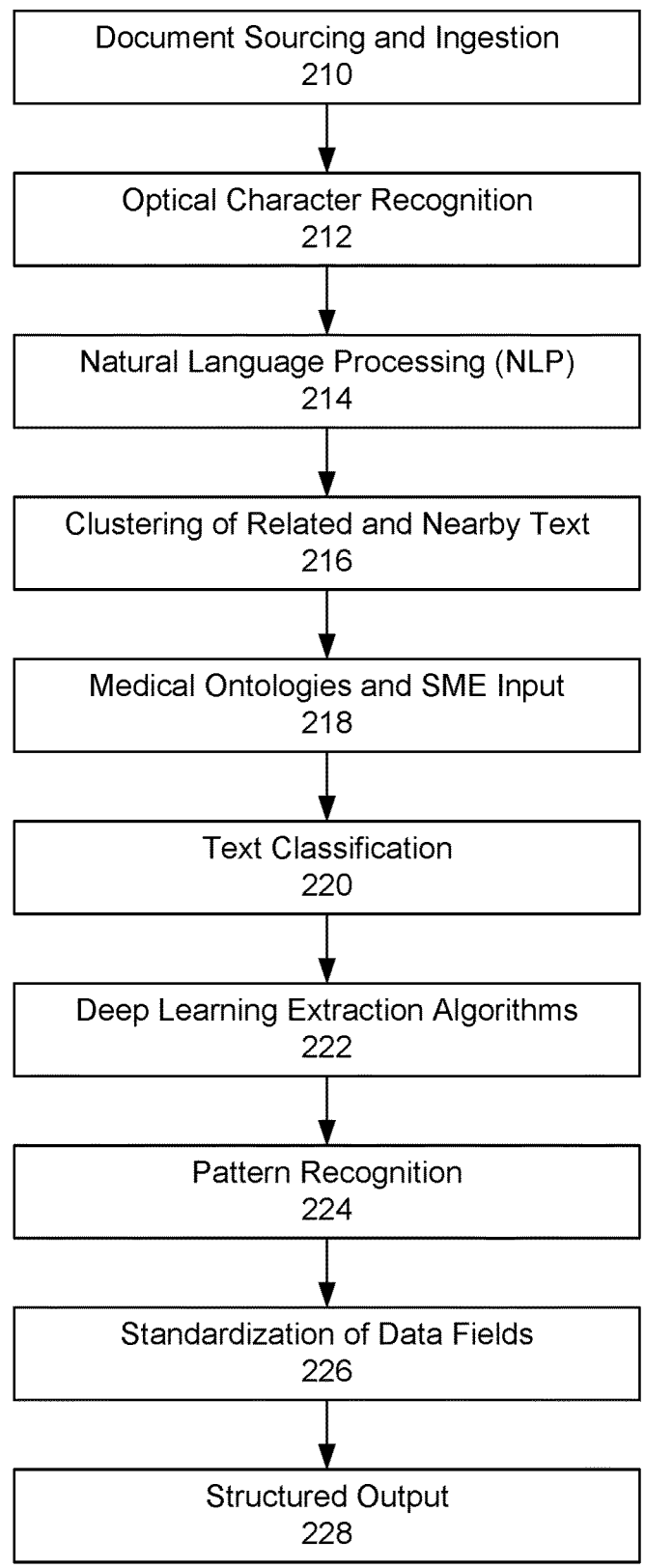
FIG. 2 is an exemplary flow diagram, according to an embodiment of the present invention.

FIG. 2 is an exemplary flow diagram, according to an embodiment of the present invention. An embodiment of the present invention may store document data in a data object, on which various "components" are applied, and output information may be stored in elements within the document's data object. According to an exemplary illustration, "components" may refer to discrete implementations of specific functionality that may be combined to produce complete solutions for a given use-case. In the context of this exemplary embodiment, components may refer to OCR, NLP, Deep Learning key-value pair extraction, etc.

Also, output information elements may contain various attributes to allow more granular analysis of the documents.

At step 210, document sourcing and ingestion may be performed. Documents may be ingested and processed according to the supported file types. This may further involve capturing metadata and identifying document characteristics.

At step 212, optical character recognition may be performed. An Optical Character Recognition component may be applied to the documents. This may involve extracting text content and spatial location in the document.

At step 214, natural language processing (NLP) may be performed. The NLP component may parse the document into segments such as phrases, sentences, paragraphs and/or other hierarchical concepts. The NLP component may also detect medical domain specific keywords, entities, phrases, etc.

At step 216, a clustering of related and nearby text may be performed. Document texts may be grouped into categories and semantic groups based on similarity measures in order to inform the Machine Learning (ML) models training. Similarity measures may refer to various methods of comparing text content for semantic/topic similarity based on a desired domain and use-case. For example, an embodiment of the present invention may determine if a given paragraph from a medical record contains a description of a patient's injury by comparing it to other known examples of patient history texts from other medical records.

At step 218, medical ontologies and SME input may be received. Existing and SME customized medical domain ontologies may further enhance the metadata associated with identified sections and entities.

At step 220, text classification may be performed. Text classification models may identify sections of text that contain information relevant to a specific medical concept.

At step 222, deep learning extraction algorithms may be executed. Deep Learning models identify and extract use-case specific entities and phrases.

At step 224, pattern recognition may be performed. Domain specific and SME informed search patterns and business logic may further filter and refine extracted information from the documents.

At step 226, standardization of data fields may be initiated. Extracted information and data fields may be converted into standardized formats for easy storage, transfer, and loading into integrated systems.

At step 228, structured output may be generated and provided. Standardized data may be exported into structured outputs for viewing and consumption by downstream users and applications. The structured output may be transmitted and/or communicated to various recipients through an interactive interface. According to another example, the structured output may be compiled into a report and/or other end product. In addition, the structured output may be transmitted to a receiving system for additional analysis and processing. The interactive interface may be supported by various browsers, applications, systems, mobile devices, etc.

While the process of FIG. 2 illustrates certain steps performed in a particular order, it should be understood that the embodiments of the present invention may be practiced by adding one or more steps to the processes, omitting steps within the processes and/or altering the order in which one or more steps are performed.

Figure 3:
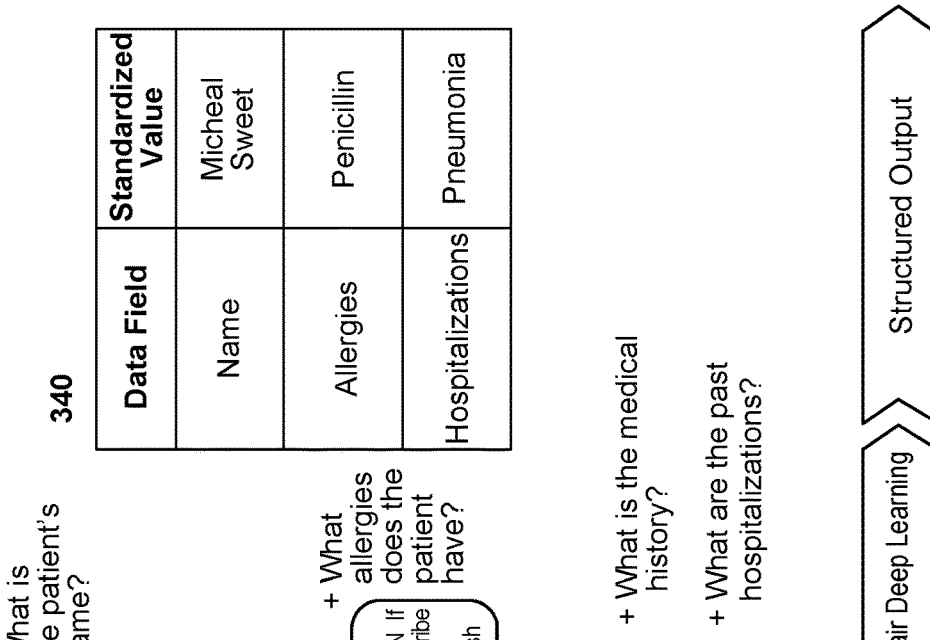
FIG. 3 is an exemplary illustration, according to an embodiment of the present invention.

FIG. 3 is an exemplary illustration, according to an embodiment of the present invention. An embodiment of the present invention may access, read and/or interpret a health care form, identify related text, leverage computer vision to group nearby text, and use deep learning models to identify fields from the text. This information may then be used to create a structured standardized output. An embodiment of the present invention may extract information in various formats including Explicit Data Extraction 310, Form Data Extraction 320 and Free Text Extraction 330.

As shown in FIG. 3, Explicit Data Extraction 310 may be performed to identify certain characteristics, such as a patient's name. In this example, an embodiment of the present invention may identify the text that is associated with the field "Patient Name" or other similar identifier.

As shown in FIG. 3, Form Data Extraction 320 may be performed. In this example, a user may seek to identify any allergies associated with the patient. The system may understand a certain document's format and identify the section that corresponds to allergies, in this example. This information may be available as templates and/or other formats based on standardized and/or customized documents.

Free Text Extraction 330 may be used to identify medical history and any past hospitalizations. As shown in FIG. 3, an embodiment of the present invention may identify an answer provided in free text format and then extract and interpret the relevant portions.

A structured output may be generated as shown by 340. The structured output may include data field and a corresponding standardized value. Other formats and additional information may be compiled.

It will be appreciated by those persons skilled in the art that the various embodiments described herein are capable of broad utility and application. Accordingly, while the various embodiments are described herein in detail in relation to the exemplary embodiments, it is to be understood that this disclosure is illustrative and exemplary of the various embodiments and is made to provide an enabling disclosure. Accordingly, the disclosure is not intended to be construed to limit the embodiments or otherwise to exclude any other such embodiments, adaptations, variations, modifications and equivalent arrangements.

The foregoing descriptions provide examples of different configurations and features of embodiments of the invention. While certain nomenclature and types of applications/hardware are described, other names and application/hardware usage is possible and the nomenclature is provided by way of non-limiting examples only. Further, while particular embodiments are described, it should be appreciated that the features and functions of each embodiment may be combined in any combination as is within the capability of one skilled in the art. The figures provide additional exemplary details regarding the various embodiments.

Various exemplary methods are provided by way of example herein. The methods described can be executed or otherwise performed by one or a combination of various systems and modules.

The use of the term computer system in the present disclosure can relate to a single computer or multiple computers. In various embodiments, the multiple computers can be networked. The networking can be any type of network, including, but not limited to, wired and wireless networks, a local-area network, a wide-area network, and the Internet.

According to exemplary embodiments, the System software may be implemented as one or more computer program products, for example, one or more modules of computer program instructions encoded on a computer-readable medium for execution by, or to control the operation of, data processing apparatus. The implementations can include single or distributed processing of algorithms. The computer-readable medium can be a machine-readable storage device, a machine-readable storage substrate, a memory device, or a combination of one or more them. The term "processor" encompasses all apparatus, devices, and machines for processing data, including by way of example a programmable processor, a computer, or multiple processors or computers. The apparatus can include, in addition to hardware, software code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communications network.

A computer may encompass all apparatus, devices, and machines for processing data, including by way of example a programmable processor, a computer, or multiple processors or computers. It can include, in addition to hardware, code that creates an execution environment for the computer program in question, e.g., code that constitutes processor firmware, a protocol stack, a database management system, an operating system, or a combination of one or more of them.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computer-readable media suitable for storing computer program instructions and data can include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While the embodiments have been particularly shown and described within the framework for conducting analysis, it will be appreciated that variations and modifications may be affected by a person skilled in the art without departing from the scope of the various embodiments. Furthermore, one skilled in the art will recognize that such processes and systems do not need to be restricted to the specific embodiments described herein. Other embodiments, combinations of the present embodiments, and uses and advantages of the will be apparent to those skilled in the art from consideration of the specification and practice of the embodiments disclosed herein. The specification and examples should be considered exemplary.

What is claimed is:

1. A computer-implemented method for analyzing at least one of structured and unstructured data, the method comprising:

identifying at least one question and at least one input file to be analyzed, wherein the at least one input file relates to a series of longitudinal medical records wherein the medical records comprise structured and unstructured image and textual medical history data for a patient over a predetermined period of time;

extracting high dimensional data from the image medical history data by applying image analysis and segmentation to the at least one input file;

applying text spatial analysis and clustering of related and nearby text to the at least one input file based on one or more similarity measures; and responsive to the text spatial analysis and clustering, applying an artificial intelligence process implementing a machine learning model to the at least one input file, the artificial intelligence process comprising the steps of:

identifying, for the at least one input file, at least one key-value pair wherein the identification is based on a medical ontology and a text classification model configured to detect information relevant to a specific medical concept;

generating, for the at least one input file, a converted file in a data format that is standardized for a plurality of input file types and a plurality of data providers and that includes at least one element; wherein the at least one element is associated with the at least one key-value pair;

training the machine learning model over the standardized data format based on a training data set and a configuration file comprising at least one of a task type, an algorithm and package type, and a plurality of features;

generating at least one expression, wherein the expression comprises an expression string in a domain-specific language;

reading, via a machine review portion of the trained machine learning model, the at least one expression; and applying, via the machine review portion of the trained machine learning model, the at least one expression to the converted file to automatically generate a structured data output responsive to the at least one question; and transmitting the structured output to one or more downstream users.

2. The method of claim 1, wherein the medical record comprises at least one medical image.

3. The method of claim 1, wherein the plurality of data providers comprise one or more of: medical doctors, hospitals, clinics and medical providers.

4. The method of claim 1, wherein the at least one element is extracted from the at least one input file through one or more of: explicit data extraction, form data extraction and free text extraction.

5. The method of claim 1, wherein the structured data output comprises a data field and a corresponding standardized value.

6. The method of claim 1, wherein the at least one input file comprises one or more of: health records, intake forms, medical history and worker's compensation.

7. The method of claim 1, wherein the key identifier and the corresponding value relate to subject matter expert (SME) medical ontology.

8. The method of claim 1, wherein text spatial analysis and clustering comprises a combination of computer vision and natural language processing (NLP) to structure an image of a medical record into one or more semantic regions.

9. The method of claim 1, wherein the at least one expression identifies one or more specific words, relationships between words, patterns or features.

10. The method of claim 1, wherein the one or more similarity measures compare text content for semantic/topic similarity based on a desired domain and use-case.

11. A computer-implemented system for analyzing at least one of structured and unstructured data, the system comprising:

an input that identifies at least one question and at least one input file to be analyzed, wherein the at least one input file relates to a series of longitudinal medical records wherein the medical records comprise structured and unstructured image and textual medical history data for a patient over a predetermined period of time; and a server configured to perform the steps of:

extracting high dimensional data from the image medical history data by applying image analysis and segmentation to the at least one input file;

applying text spatial analysis and clustering of related and nearby text to the at least one input file based on one or more similarity measures;

responsive to the text spatial analysis and clustering, applying an artificial intelligence process implementing a machine learning model to the at least one input file, the artificial intelligence process comprising:

identifying, for the at least one input file, at least one key-value pair wherein the identification is based on a medical ontology and a text classification model configured to detect information relevant to a specific medical concept;

generating, for the at least one input file, a converted file in a data format that is standardized for a plurality of input file types and a plurality of data providers and that includes at least one element; wherein the at least one element is associated with the at least one key-value pair;

training the machine learning model over the standardized data format based on a training data set and a configuration file comprising at least one of a task type, an algorithm and package type, and a plurality of features;

generating at least one expression, wherein the expression comprises an expression string in a domain-specific language;

reading, via a machine review portion of the trained machine learning model, the at least one expression; and applying, via the machine review portion of the trained machine learning model, the at least one expression to the converted file to automatically generate a structured data output responsive to the at least one question; and transmitting the structured output to one or more downstream users.

12. The system of claim 11, wherein the medical record comprises at least one medical image.

13. The system of claim 11, wherein the plurality of data providers comprise one or more of: medical doctors, hospitals, clinics and medical providers.

14. The system of claim 11, wherein the at least one element is extracted from the at least one input file through one or more of: explicit data extraction, form data extraction and free text extraction.

15. The system of claim 11, wherein the structured data output comprises a data field and a corresponding standardized value.

16. The system of claim 11, wherein the at least one input file comprises one or more of: health records, intake forms, medical history and worker's compensation.

17. The system of claim 11, wherein the key identifier and the corresponding value relate to subject matter expert (SME) medical ontology.

18. The system of claim 11, wherein text spatial analysis and clustering comprises a combination of computer vision and natural language processing (NLP) to structure an image of a medical record into one or more semantic regions.

19. The system of claim 11, wherein the at least one expression identifies one or more specific words, relationships between words, patterns or features.

20. The system of claim 11, wherein the one or more similarity measures compare text content for semantic/topic similarity based on a desired domain and use-case.

* * * * *